US010251722B1

(12) United States Patent
Allen et al.

(10) Patent No.: US 10,251,722 B1
(45) Date of Patent: Apr. 9, 2019

(54) STEREOTAXIC BRAIN IMPLANT SYSTEM FOR LARGE ANIMALS

(71) Applicants: Timothy Allen, Coral Gables, FL (US); Adam Draper, Miami, FL (US); Aaron Mattfeld, Miami, FL (US)

(72) Inventors: Timothy Allen, Coral Gables, FL (US); Adam Draper, Miami, FL (US); Aaron Mattfeld, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 16/133,268

(22) Filed: Sep. 17, 2018

(51) Int. Cl.
| | | |
|---|---|---|
| *A61B 90/11* | (2016.01) | |
| *A61B 34/10* | (2016.01) | |
| *A61B 5/00* | (2006.01) | |
| A61B 90/00 | (2016.01) | |
| A61B 34/00 | (2016.01) | |
| A61F 2/28 | (2006.01) | |

(52) U.S. Cl.
CPC ............ *A61B 90/11* (2016.02); *A61B 5/4064* (2013.01); *A61B 34/10* (2016.02); *A61B 5/6864* (2013.01); *A61B 34/70* (2016.02); *A61B 2034/107* (2016.02); *A61B 2034/108* (2016.02); *A61B 2090/374* (2016.02); *A61F 2/2875* (2013.01)

(58) Field of Classification Search
CPC . A61B 90/11; A61B 5/4064; A61B 2034/107; A61B 2034/108; A61B 34/70; A61B 2090/374; A61B 5/6864; A61B 2090/103; A61B 90/10; A61B 2017/3405; A61B 2017/3407; A61B 2017/3411; A61F 2/2875; Y10S 439/909; A61N 1/05; A61N 1/0504; A61N 1/0526; A61N 1/0529; A61N 1/0541; A61N 1/0543; A61N 1/0546; A61N 1/0531; A61N 1/0534; A61N 1/0536; A61N 1/0539
See application file for complete search history.

(56) References Cited

U.S. PATENT DOCUMENTS

| | | |
|---|---|---|
| 3,016,899 A | 1/1962 | Stenvall |
| 3,021,842 A | 2/1962 | Flood |
| 3,061,936 A | 11/1962 | Dobbeleer |
| 3,223,087 A | 12/1965 | Vladyka et al. |
| 3,357,431 A | 12/1967 | Newell |
| 3,374,548 A | 3/1968 | Romney |
| 3,384,086 A | 5/1968 | Rocha-Miranda et al. |
| 3,457,922 A | 7/1969 | Ray |
| 3,508,552 A | 4/1970 | Hainault |
| 3,817,249 A | 6/1974 | Nicholson |
| 4,228,799 A | 10/1980 | Anichkov et al. |
| 4,341,220 A | 7/1982 | Perry |

(Continued)

*Primary Examiner* — David C Eastwood
(74) *Attorney, Agent, or Firm* — Saliwanchik, Lloyd & Eisenschenk

(57) ABSTRACT

A stereotactic system with customizable and interoperable components for implantation of intracranial implants is provided. The stereotactic system can include a NeuroHat stereotactic device that attaches directly to the skull of an animal subject to protect chronic intracranial implants without interfering with the normal activities of the animal subject. The stereotactic system can also include a drill guide for accurate placement of burr holes and implant shuttles designed to be interoperable with other components of the NeuroHat stereotactic device for accurate placement and secureability.

19 Claims, 6 Drawing Sheets

(56) References Cited

U.S. PATENT DOCUMENTS

| | | | |
|---|---|---|---|
| 4,350,159 A | 9/1982 | Gouda | |
| 4,386,602 A | 6/1983 | Sheldon et al. | |
| 4,463,758 A | 8/1984 | Patil et al. | |
| 4,592,352 A | 6/1986 | Patil | |
| 4,608,977 A | 9/1986 | Brown | |
| 4,618,978 A | 10/1986 | Cosman | |
| 4,706,665 A | 11/1987 | Gouda | |
| 4,834,089 A | 5/1989 | Koivukangas et al. | |
| 4,961,422 A * | 10/1990 | Marchosky | A61F 7/00 607/99 |
| 5,004,457 A | 4/1991 | Wyatt et al. | |
| 5,006,122 A | 4/1991 | Wyatt et al. | |
| 5,030,223 A | 7/1991 | Anderson et al. | |
| 5,047,036 A | 9/1991 | Koutrouvelis | |
| 5,080,662 A | 1/1992 | Paul | |
| 5,116,345 A | 5/1992 | Jewell et al. | |
| 5,143,076 A | 9/1992 | Hardy et al. | |
| 5,147,372 A | 9/1992 | Nymark et al. | |
| 5,154,723 A | 10/1992 | Kubota et al. | |
| 5,163,430 A | 11/1992 | Carol | |
| 5,176,689 A | 1/1993 | Hardy et al. | |
| 5,201,742 A | 4/1993 | Hasson | |
| 5,257,998 A | 11/1993 | Ota et al. | |
| 5,263,956 A * | 11/1993 | Nobles | A61B 90/11 606/1 |
| 5,308,352 A | 5/1994 | Koutrouvelis | |
| 5,441,505 A | 8/1995 | Nakamura | |
| 5,665,095 A | 9/1997 | Jacobson | |
| 5,682,892 A | 11/1997 | Selder et al. | |
| 5,690,108 A | 11/1997 | Chakeres | |
| 5,752,962 A | 5/1998 | D'Urso | |
| 5,776,143 A | 7/1998 | Adams | |
| 5,782,645 A * | 7/1998 | Stobie | A61N 1/02 439/289 |
| 5,957,934 A | 9/1999 | Rapoport | |
| 5,984,930 A | 11/1999 | Maciunas et al. | |
| 6,011,996 A | 1/2000 | Gielen et al. | |
| 6,110,182 A | 8/2000 | Mowlai-Ashtiani | |
| 6,132,437 A | 10/2000 | Omurtag et al. | |
| 6,221,082 B1 | 4/2001 | Marino et al. | |
| 6,261,299 B1 | 7/2001 | Chakeres | |
| 6,327,491 B1 | 12/2001 | Franklin et al. | |
| 6,491,699 B1 | 12/2002 | Henderson et al. | |
| 6,529,765 B1 | 3/2003 | Franck et al. | |
| 6,589,254 B2 | 7/2003 | Fontenot | |
| 6,689,142 B1 | 2/2004 | Tremaglio, Jr. et al. | |
| 6,716,215 B1 * | 4/2004 | David | A61B 17/1622 433/116 |
| 6,989,015 B2 | 1/2006 | Daum et al. | |
| 7,329,262 B2 | 2/2008 | Gill | |
| 7,366,561 B2 | 4/2008 | Mills et al. | |
| 7,497,863 B2 | 3/2009 | Solar et al. | |
| 7,559,935 B2 | 7/2009 | Solar et al. | |
| 7,603,161 B2 | 10/2009 | Wurmfeld et al. | |
| 7,636,596 B2 | 12/2009 | Solar | |
| 7,744,606 B2 | 6/2010 | Miller et al. | |
| 7,776,048 B2 | 8/2010 | Neubauer et al. | |
| 7,787,936 B2 | 8/2010 | Kressy et al. | |
| 7,879,045 B2 | 2/2011 | Gielen et al. | |
| 7,892,243 B2 | 2/2011 | Stuart | |
| 8,092,495 B2 | 1/2012 | Boulis et al. | |
| 8,099,150 B2 | 1/2012 | Piferi et al. | |
| 8,298,245 B2 | 10/2012 | Li et al. | |
| 8,374,677 B2 | 2/2013 | Piferi et al. | |
| 8,414,597 B2 | 4/2013 | Kao et al. | |
| 8,435,250 B2 * | 5/2013 | Yoon | A61N 1/0529 310/323.06 |
| 8,548,569 B2 | 10/2013 | Piferi et al. | |
| 8,617,180 B2 | 12/2013 | Thiran et al. | |
| 8,657,761 B2 | 2/2014 | Kim et al. | |
| 8,744,552 B2 | 6/2014 | Akuzawa et al. | |
| 8,747,331 B2 | 6/2014 | Luginbuhl et al. | |
| 8,747,419 B2 * | 6/2014 | Solar | A61B 90/11 606/130 |
| 8,771,290 B2 | 7/2014 | Mitchell et al. | |
| 8,818,490 B2 | 8/2014 | Martens et al. | |
| 8,944,069 B2 * | 2/2015 | Miller | A61B 10/025 128/852 |
| 9,061,133 B2 | 6/2015 | Wurster et al. | |
| 9,131,948 B2 | 9/2015 | Fang et al. | |
| 9,192,446 B2 | 11/2015 | Piferi et al. | |
| 9,289,270 B2 | 3/2016 | Gielen et al. | |
| 9,345,875 B2 | 5/2016 | Appenrodt et al. | |
| 9,387,008 B2 | 7/2016 | Sarvestani et al. | |
| 9,468,751 B2 | 10/2016 | Bonde | |
| 9,498,290 B2 | 11/2016 | Piferi et al. | |
| 9,707,049 B1 | 7/2017 | Allen et al. | |
| 2003/0187351 A1 | 10/2003 | Franck et al. | |
| 2004/0243146 A1 * | 12/2004 | Chesbrough | A61B 90/11 606/130 |
| 2005/0085719 A1 * | 4/2005 | Franklin | A61B 90/11 600/424 |
| 2005/0124990 A1 * | 6/2005 | Teague | A61B 17/1735 606/53 |
| 2005/0283203 A1 * | 12/2005 | Flaherty | A61B 5/04001 607/48 |
| 2006/0079886 A1 | 4/2006 | Orszulak et al. | |
| 2006/0079887 A1 | 4/2006 | Buysse et al. | |
| 2006/0229641 A1 * | 10/2006 | Gupta | A61B 17/3403 606/130 |
| 2007/0078306 A1 | 4/2007 | Allison et al. | |
| 2007/0106305 A1 * | 5/2007 | Kao | A61B 90/11 606/130 |
| 2007/0203538 A1 | 8/2007 | Stone et al. | |
| 2007/0203539 A1 | 8/2007 | Stone et al. | |
| 2007/0203543 A1 | 8/2007 | Stone et al. | |
| 2007/0203546 A1 | 8/2007 | Stone et al. | |
| 2007/0233158 A1 * | 10/2007 | Rodriguez | A61N 1/0531 606/130 |
| 2007/0296310 A1 * | 12/2007 | Kim | A61B 5/04001 310/338 |
| 2008/0171930 A1 | 7/2008 | Abolfathi et al. | |
| 2008/0255583 A1 * | 10/2008 | Gielen | A61B 17/3403 606/130 |
| 2009/0112278 A1 * | 4/2009 | Wingeier | A61B 5/6864 607/45 |
| 2009/0171184 A1 * | 7/2009 | Jenkins | A61B 5/7435 600/411 |
| 2009/0264899 A1 * | 10/2009 | Appenrodt | A61N 1/0529 606/130 |
| 2010/0042111 A1 * | 2/2010 | Qureshi | F16M 11/14 606/130 |
| 2010/0179564 A1 * | 7/2010 | Mitchell | A61B 90/11 606/130 |
| 2011/0190789 A1 * | 8/2011 | Thiran | A61B 17/1739 606/130 |
| 2011/0295271 A1 * | 12/2011 | Kao | A61B 90/11 606/130 |
| 2011/0319913 A1 * | 12/2011 | Labadie | A61B 17/3403 606/130 |
| 2013/0030408 A1 | 1/2013 | Piferi et al. | |
| 2013/0053867 A1 * | 2/2013 | Gowda | A61B 17/00234 606/130 |
| 2013/0072876 A1 * | 3/2013 | Pretre | A61M 25/04 604/175 |
| 2013/0211424 A1 * | 8/2013 | Thiran | A61B 90/11 606/130 |
| 2014/0378775 A1 * | 12/2014 | Bowman | A61B 5/4064 600/235 |
| 2015/0031982 A1 * | 1/2015 | Piferi | A61N 1/0534 600/411 |
| 2015/0133761 A1 * | 5/2015 | Vetter | H01R 43/26 600/378 |
| 2015/0202011 A1 * | 7/2015 | Gowda | A61B 17/3423 606/130 |
| 2015/0320560 A1 * | 11/2015 | Mulliken | A61B 90/10 623/17.19 |
| 2016/0000448 A1 * | 1/2016 | Houssiere | A61B 17/1622 606/130 |
| 2016/0367331 A1 | 12/2016 | Nelson et al. | |
| 2017/0020623 A1 | 1/2017 | Glossop | |

(56) References Cited

U.S. PATENT DOCUMENTS

2018/0110568 A1* 4/2018 Lenarz .................. A61B 90/11
2018/0177562 A1* 6/2018 Allen .................... A61B 90/11
2018/0325412 A1* 11/2018 Bankiewicz .......... A61B 5/055

* cited by examiner

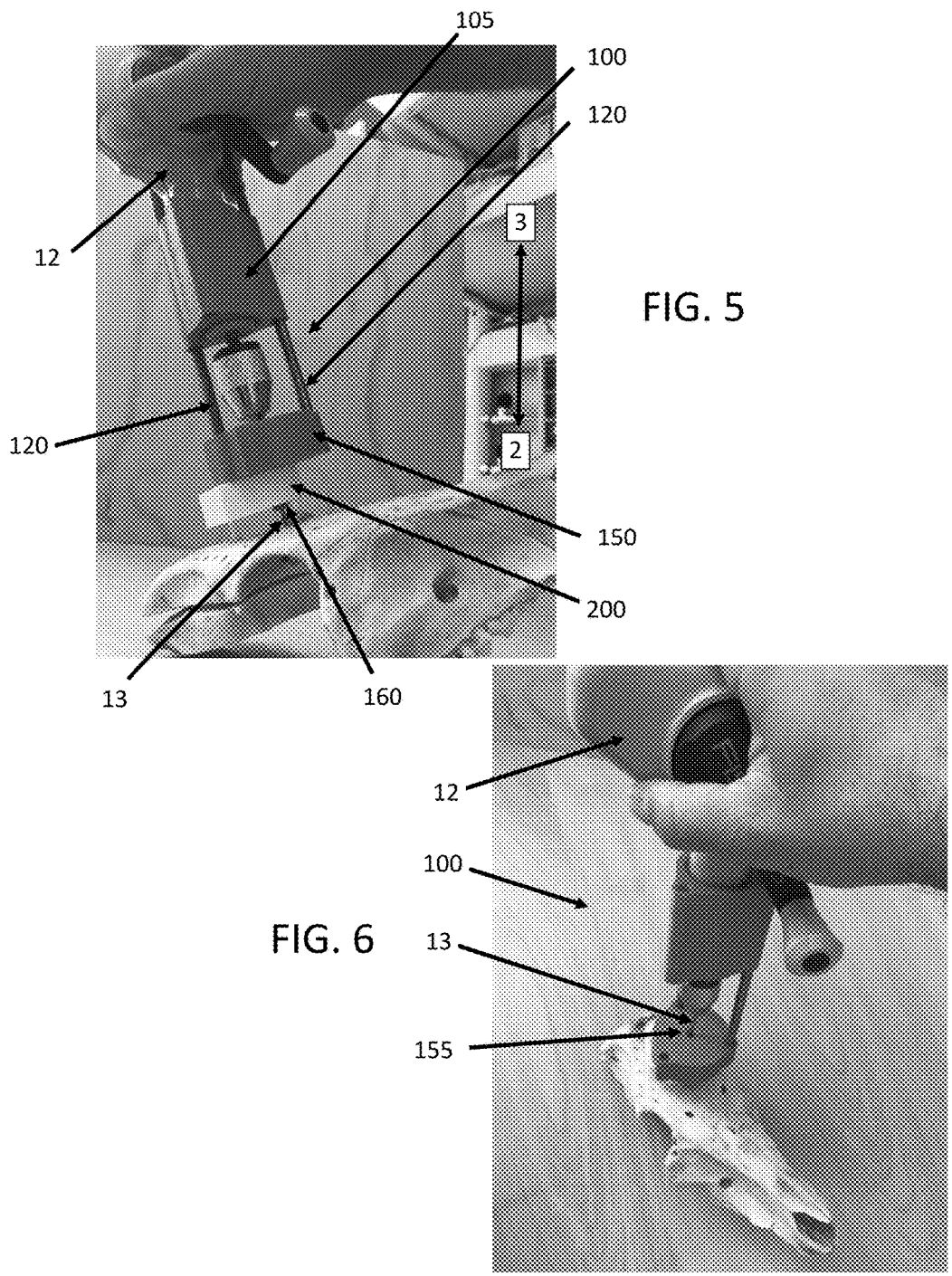

STEREOTAXIC BRAIN IMPLANT SYSTEM FOR LARGE ANIMALS

BACKGROUND

To understand complex cognition, neurophysiological studies of large-scale networks of neurons are necessary. While human studies using fMRI have shown evidence for task-related networks across the brain, these studies lack the ability to evaluate mechanisms at the cellular level. Similar brain networks are assumed to support cognition across mammals (Lu et al., 2012), but the most common rodent and primate models present challenges in achieving high-volume multisite single-unit recordings in behaving animals.

The domestic pig (*Sus scrofa domesticus*) has a large brain and thick skull, allowing for large implants targeting multiple brain regions. It has been shown that domestic pigs can be trained to perform a conditional associative learning paradigm. Behavioral performance of the domestic pig has also been shown to mirror that observed in humans performing the same task.

To fully understand the neural network associated with a behavior, untethered, intracranial electrode probe assemblies are implanted into different regions of a pig brain to obtain large-scale electrophysiological recordings of brain activity during performance of the task. Stereotactic devices are often used to guide and accurately place such intracranial devices. Stereotactic surgical procedures to place these types of devices within a body or tissue can require accuracy to within millimeters or even micrometers. Such accuracy can depend upon the stereotactic device used to guide the intra-body devices to specific points in the tissue, particularly in the brain.

The differences in anatomy, size, orientation of features, and points of attachment necessitate different types of stereotactic devices for different species. Unfortunately, the current methods for placement of intracranial devices in large animals, such as the domestic pig, involve the use of large animal stereotaxic head fixtures, which require tight head restraints that penetrate the skin and contact the skull in multiple locations. This method also requires the head to be leveled and oriented relative to the stereotaxic head fixture.

Once emplaced, electrode assemblies are often permanent or semi-permanent for long term treatment, therapies, or research and often have externally exposed ends protruding outside the skull. These exposed ends need to be supported to ensure that the intra-cranially placed devices remain in position. Those that provide a direct conduit into the brain need to be covered to ensure that undesirable materials are not introduced into the brain. This makes intracranial devices implanted in animals particularly problematic, since normal activities of the animal can cause collisions with the exposed ends and, in some cases, the animal can actively attempt to remove or displace the exposed ends.

BRIEF SUMMARY

Embodiments of the subject invention address the problems of accurately implanting and supporting intracranial devices on a subject (e.g., large animal species) by providing a stereotactic system that can be at least partly customized to the skull anatomy of a specific type of subject (e.g., the domestic pig, *Sus scrofa domesticus*). Components of the stereotactic system allow intracranial implant devices, such as electrode probe assemblies, to be pre-arranged to the appropriate direction and depth before implantation. Advantageously, certain components of the stereotactic system, which includes components referred to collectively as a "NeuroHat," can be attached to the skull to support and contain the exposed ends of the intracranial devices. The stereotactic system being customized for a specific species can be used on individuals within the species with higher accuracy and more comfortable and secure permanent or semi-permanent placement on the skull. The stereotactic system is particularly advantageous with larger animals because it is minimally invasive, causing less physical damage to the animal and can require fewer measurements and adjustments of the head during surgery, which saves time and minimizes errors.

Prior to a neurosurgical procedure, it is not uncommon to obtain a 3-dimensional (3-D) image of the brain, skull, and other structures, so that placement of intracranial devices can be pre-planned. Such 3-D images can also be used to customize components of the stereotactic system and pre-plan the placement of intracranial devices, using the components of the customized stereotactic system. There are a variety of methods and techniques available for obtaining 3-D images and the invention is not limited to any particular method or technique.

Embodiments of a stereotactic system of the subject invention include a skull guide that initially aligns to specific coordinates in the anterior-posterior and medial-lateral directions of the animal skull. The skull guide can have a plurality of guide holes and two or more stand-off posts that are implanted in and affixed to the skull. The skull guide can be utilized initially to align a drill guide and drill therein for making burr holes in the skull and, later, for the subsequent accurate placement of intracranial devices through one or more guide holes and into the burr holes.

Embodiments of a NeuroHat device, a part of the stereotactic system, can include components comprising a lower-housing that fits around the skull guide to protect the intracranial implants; a mounting plate having a plurality of conformations to accommodate attachment of various devices to the NeuroHat and the intracranial implants, and an upper-housing that can attach to the lower-housing to seal the implant system. The upper-housing can further act as a dampener to minimize the effects of contact with the NeuroHat. Once installed, access to internal components and electrodes can be achieved through a removable access plate or by removal of the upper housing in the NeuroHat.

In summary, by using general physiological characteristics, a stereotactic system of the subject invention can be customized or adapted for use with a specific species, particularly large animal species such as the domestic pig. Advantageously, customized components allow configuration and placement of intracranial implants to be determined prior to actual implantation within a subject. The ability to customize the components of the stereotactic device to interface with the skull surface provides greater options and accuracy in implant placement for a specific species. The housing components of the stereotactic system provide protection and access to the implants after placement.

It should be noted that this Brief Summary is provided to generally introduce the reader to one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. Thus, understanding that these drawings depict only typical embodiments of the invention and are not therefore to be considered as limiting in scope, the invention will be described and explained with additional specificity and detail through the use of the accompanying drawings in which:

FIG. 5 is an illustration of embodiments of a drill guide, with a drill therein, and a skull guide that has been affixed to a representative domestic pig skull. In this side view, the stand-off posts are seen affixed to the skull.

FIG. 6 is an illustration of embodiments of a drill guide, with a drill therein, and a skull guide that has been affixed to a representative domestic pig skull. In this view, the drill bit can be seen going through the guide hole of the drill guide.

FIG. 7 shows an implant shuttle that implants to a specific depth.

DETAILED DESCRIPTION

Figure 1:
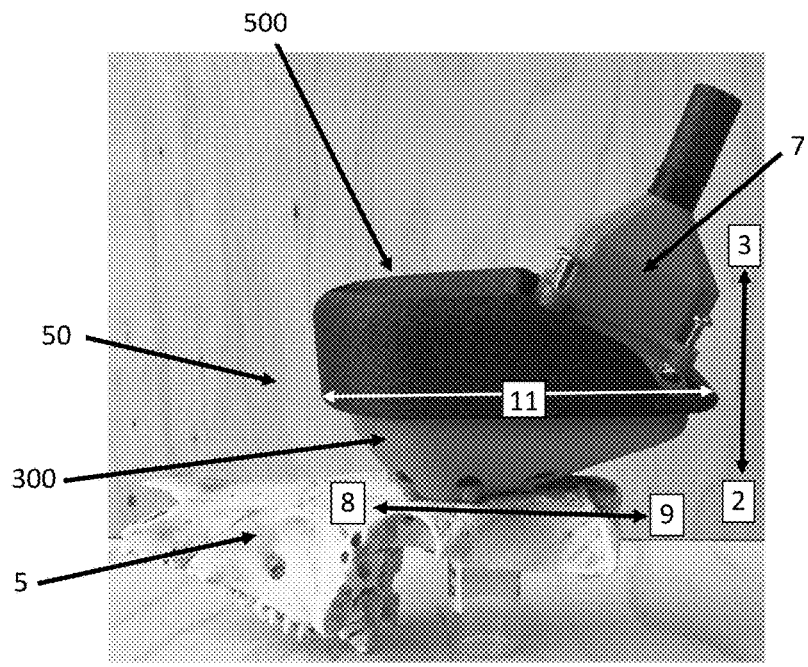
FIG. 1 shows an embodiment of a NeuroHat stereotactic device, according to the subject invention, affixed, by way of example, to a representative skull of a domestic pig. In this view, the NeuroHat stereotactic device is shown with a secondary device connected to the mounting plate.

Embodiments of the subject invention pertain to a stereotactic system useful for implanting and securing intracranial or other types of implants. More specifically, a stereotactic system with one or more components that can be customized for implanting and securing intracranial implants into the brain of a specific species are provided. The components of a stereotactic system can include customized components for increased accuracy in implant placement.

The following description will disclose that embodiments of the subject invention are particularly useful in the field of neurosurgical techniques, in particular the implantation of intracranial devices. However, embodiments of the subject invention are not limited to just neurosurgical applications or only to the implantation of intracranial devices. A person with skill in the art will be able to recognize numerous other uses that would be applicable to the devices and methods of the subject invention. Thus, while the subject application describes, and many of the terms herein relate to, a use for implantation of intracranial devices through the skull of a subject, other uses and modifications apparent to a person with skill in the art and having benefit of the subject disclosure are contemplated to be within the scope of the present invention.

In the description that follows, a number of terms are used in relation to the subject invention. In order to provide a clear and consistent understanding of the specification and claims, including the scope to be given such terms, the following definitions are provided.

The terms "subject" and "specific species", as used herein, describes an animal, including mammals, to which the devices and methods of the present invention can be applied and that can benefit from such application. This can include mammalian species such as, but not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. It can also include patients that range in age from neonates to elderly.

The terms "intracranial implant" or "implant," as used herein, are merely for literary convenience. These terms can encompass any tool, mechanism, or device that can be permanently or temporarily inserted, implanted, installed, or otherwise introduced into or onto a subject in need of such treatment.

Likewise, the terms "brain" and "brain tissue" as used herein are merely for literary convenience. Any tissue to which the embodiments of the subject invention can be applied and useful is considered to be encompassed by these terms.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

As used herein, the terms "longitude" or "longitudinal length" refer to the longitudinal measurement or the distance extending along the long axis. For example, the longitude or longitudinal length of a NeuroHat stereotactic system is the distance or direction between the anterior end and the proximal end.

The term "about," as used herein, is defined as at least close to a given value or either end of a range as is necessary to cover manufacturing variances, equipment tolerances, and normal variances in material, as understood by those skilled in the art. Several of the components described herein are intended to operably connect, at least temporarily. As such, it should be understood that the dimensions provided will vary from the given value sufficient to allow the operable connection of those components and maintain the necessary accuracy.

It is to be understood that the figures and descriptions of embodiments of the present invention have been simplified to illustrate the elements that are relevant for a clear understanding of the invention, while eliminating, for purposes of clarity, other elements that may be well known. Those of ordinary skill in the art will recognize that other elements may be desirable and/or required in order to implement the present invention. However, because such elements are well known in the art, and because they do not facilitate a better understanding of the present invention, a detailed discussion of such elements is not provided herein.

Reference is made throughout the application to the "proximal end," "proximal side," "proximal direction," and "distal end," "distal side," or "distal direction." As used herein, the term "proximal" refers to the end, side or direction that is placed nearest to a subject when in use. For example, the end of a drill guide that contacts the skull guide affixed to a subject is the proximal end, as it is the surface that is closest to a subject during use. Conversely, the term "distal" refers to the end, side, or direction that is furthest away from the proximal end or that is directed away or furthest from a subject during use.

Embodiments of the present invention are more particularly described in the following examples that are intended to be illustrative only because numerous modifications and variations therein will be apparent to those skilled in the art. As used in the specification and in the claims, the singular for "a," "an" and "the" include plural referents unless the context clearly dictates otherwise.

Reference will be made to the attached Figures on which the same reference numerals are used throughout to indicate the same or similar components. For the purposes of illustration, certain embodiments of the invention are shown in the Figures and described herein relative to a representative skull 5 of a domestic pig (Sus scrufus demesticus). It should be understood that, in actual use, embodiments of the subject invention are intended to be employed with a living subject. With reference to the attached Figures, which show certain embodiments of the subject invention, it can be seen in FIG. 4 that in an embodiment, a stereotactic system 10 can include a NeuroHat device 50, intracranial implants configured as implant shuttles 75, and a drill guide. A NeuroHat stereotactic device (hereinafter "NeuroHat" or "NeuroHat device") can include a skull guide 200 that can be directly attached to the skull 5 of a subject, a lower housing 300 that can be positioned around the skull guide to protect the implant shuttles 75, and an upper housing 500. The lower-housing can also have a mounting socket 400 thereon, that opens in a distal direction 3, with various conformations 420 that permit attachment of secondary devices 7 to the NeuroHat device and implants. The upper-housing 500 can be placed over and around the lower-housing to cover the distal side of the lower-housing, protect the implant shuttles, and act as a shock-absorber to minimize the effects of collisions or other contact with the NeuroHat device. A drill guide 100, of the stereotactic system 50 can include a drill support 105 operably connected to a jig 150. The jig can include a post 160 that engages with the skull guide 200 to position a drill and a drill bit therein in the correct location for making a burr-hole in the skull.

Figure 2:
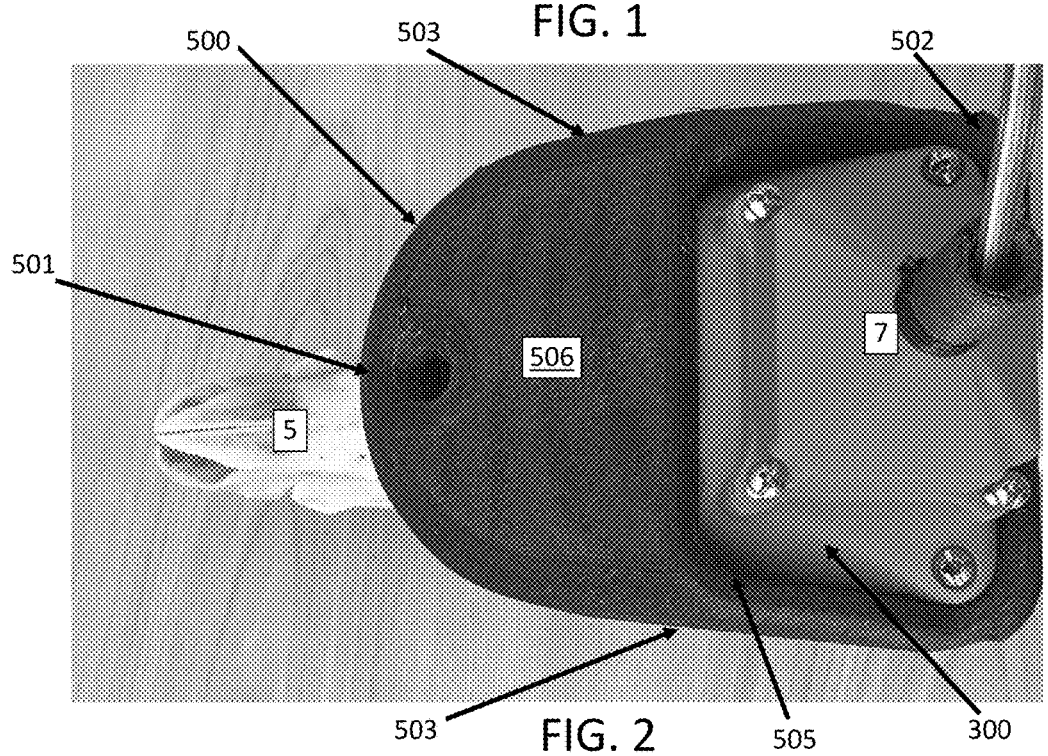
FIG. 2 shows a top plan view of an embodiment of a NeuroHat stereotactic device, according to the subject invention, affixed, by way of example, to a representative skull of a domestic pig. The NeuroHat stereotactic device is shown with a secondary device connected to the mounting plate.

With regard to the Figures, it can be seen in FIGS. 1 and 2 how an embodiment of a NeuroHat device 50 is affixed to the skull 5 of a subject. It can be advantageous, though not required, for the components of a NeuroHat device to be offset towards the neck of the subject. For example, the longitudinal length 8 of the NeuroHat device can run in an anterior 8 to a posterior 9 direction. This minimizes contact during normal activity of the animal, facilitates the maintenance of the NeuroHat after installation, and provides access for attachment of secondary devices 7.

Figure 3:
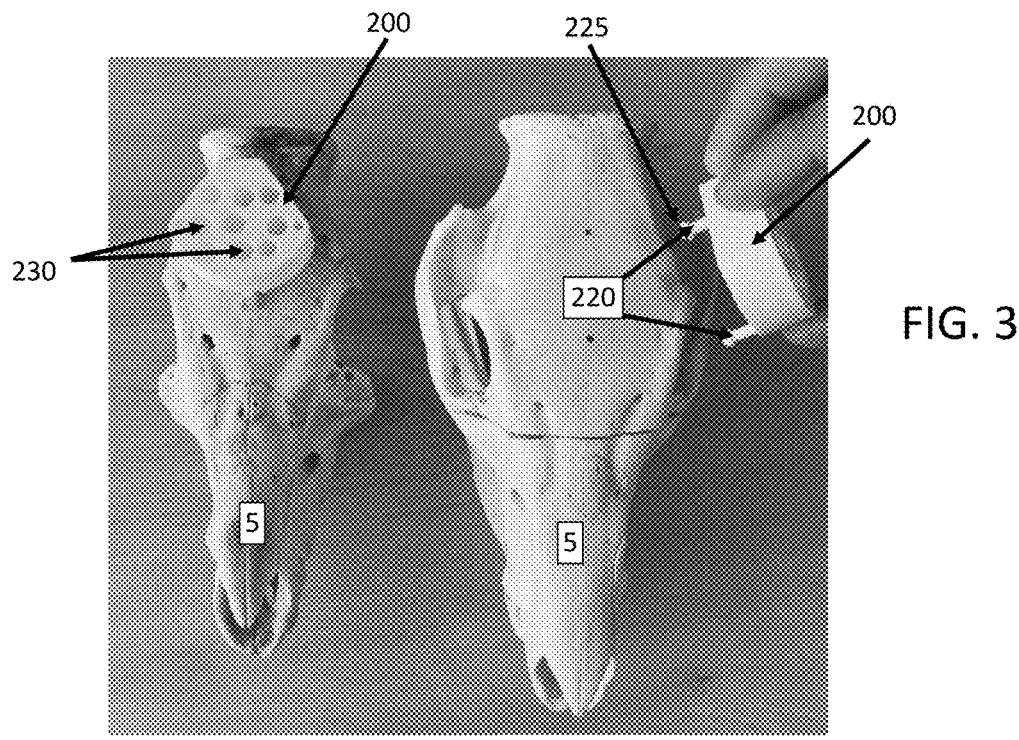
FIG. 3 illustrates embodiments of a skull guide and the stand-off posts, according to the subject invention, which can be fixedly attached to the skull of a large animal. Also shown are the representative skulls of two domestic pigs where the one on the right shows the points of attachment for the stand-off posts and the one on the left shows a skull guide with stand-off posts affixed to a representative skull.

Initially, the skull guide 200 can be attached to the skull 5 utilizing specific anterior-posterior and medial-lateral coordinates. Once the proper position for the skull guide has been determined, stand-off posts 220, located on the proximal side 2 of the skull guide, such as shown, for example, in the right-side image in FIG. 3, can be fixedly attached to the skull of the subject. The use of stand-off posts can be advantageous because it requires a minimally invasive procedure for attachment. In one embodiment, the stand-off posts are implanted into the skull. In another embodiment, the stand-off posts are fixedly or removably attached to the surface of the skull with, for example, methyl methacrylate or other biocompatible adhesive. In still another embodiment, some combination of implantation and adhesion are employed to fixedly attach the stand-off posts to the skull. In a particular embodiment, the stand-off posts have one or more surface enhancements 225 that aid or can be used to secure the stand-off posts to the skull. A surface enhancement can include, but is not limited to, extensions from or indentations in the stand-off posts that can interact with an adhesive to secure the stand-off post to the skull. FIG. 3, right-side, shows an example of a surface enhancement and FIG. 5 shows an example of a surface enhancement used with an adhesive to affix the stand-off post to the skull 5.

Figure 4:
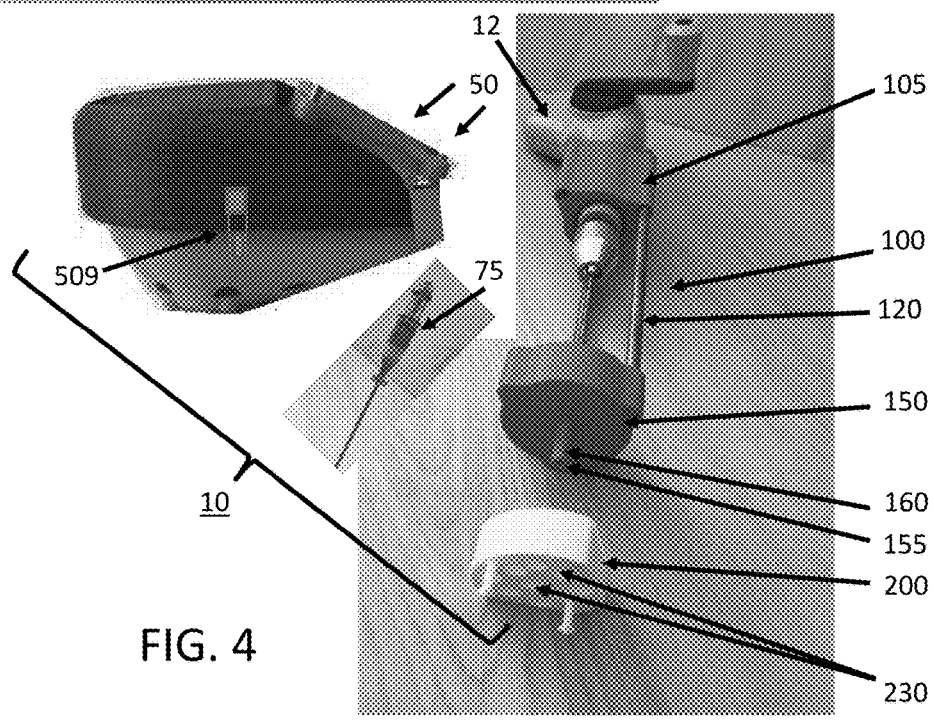
FIG. 4 illustrates an embodiment of a stereotactic system, according to the subject invention, that includes a NeuroHat stereotactic device, a drill guide, and a skull guide. The drill guide here is shown with a manual drill arranged in the drill support.
Figure 10:
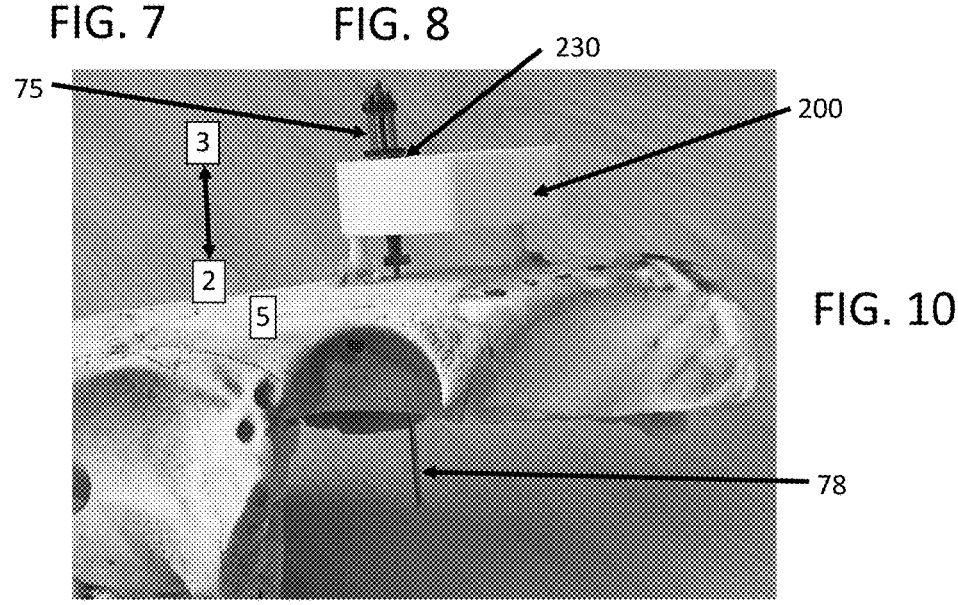
FIG. 10 shows an embodiment of a skull guide, according to the subject invention, affixed to a representative skull with an implant shuttle engaged with a guide hole in the skull guide. The electrode on the implant shuttle is shown going through a burr hole and into the brain case of the representative skull.

It can be beneficial for the skull guide to be as small as possible. In one embodiment, the skull guide is narrower laterally than the surface of the skull to which it is attached. For example, FIG. 10 shows a skull guide that fits between and does not overlap the eye sockets of the subject. Embodiments of a skull guide 200 can include at least one, more commonly, a plurality of pilot holes 230, which can serve two functions. Initially, the pilot holes are used with the drill guide to align a drill bit with the location where a burr-hole is to be drilled in the skull. This will be discussed in more detail below; but, FIG. 4 illustrates a post 160 on a drill guide configured to fit into or match the shape of the pilot hole it is to be inserted into. After the one or more burr-holes have been drilled, the one or more pilot holes can be used to position and support one or more implant shuttles 75. FIG. 10 illustrates one example of a pilot hole in which an implant shuttle is positioned and supported.

Typically, intracranial implants are positioned directly into brain tissue after first reviewing and analyzing one or more images of the tissue. The images can be a 2- or 3-dimensional image on which distances and relative positions can be determined. The depth, direction, and other data regarding the placement of the implant can be determined by reviewing the image prior to the implantation procedure. Using the same or similar information, the positioning of the skull guide and the stand-off posts thereon can be customized to an individual and a given procedure.

In one embodiment, a skull guide is customized to have pilot holes 230 in the specific locations required for the placement of cranial implants. As discussed below, the location of the pilot holes can determine where a burr-hole is ultimately drilled into the skull, which can subsequently determine where a cranial implant is located in an underlying tissue. A skull guide and the location of the pilot holes therein can be customized to a particular subject and/or procedure by any of a variety of techniques known to those with skill in the art. If necessary, the positions and lengths of the stand-off posts can also be customized to an individual and/or procedure to ensure the exact depth for the subsequently placed cranial implants. Additive manufacturing techniques (a.k.a., 3D printing) can be particularly useful because of the accuracy, economy, and speed at which skull guides and other stereotactic system components can be made for individual subjects. This does not preclude the use of Computer Numerical Control (CNC) methods, molding, or other techniques capable of providing the customization and precision necessary for the placement of pilot holes. In one embodiment, a pilot hole has a diameter of between about 7 mm and about 8 mm. In a specific embodiment, a pilot hole has a diameter of about 7.5 mm.

It was mentioned above that images of a tissue are often obtained prior to a procedure, which are used to determine positioning of cranial implants or implant shuttles 75. Once the positions have been determined, a burr-hole must be drilled through the skull to place each intracranial implant. The angle and position of the burr-hole must be exact to ensure precise placement in the tissue of the intracranial implant. A stereotactic system 10 of the subject invention can include a drill guide 100. In one embodiment, the drill guide can be used with a skull guide to ensure precise placement of one or more burr-holes.

A drill guide 100 can both support a drill and provide accurate positioning of the drill bit. One embodiment of a drill guide has a drill support 105 at the distal end 3 and a jig 150 at the proximal end 2, as shown, for example, in FIG. 4. The drill support 105 can operably connect to the jig 150 at an appropriate distance by one or more supports 120, an example of which is shown in FIGS. 4 and 5. A drill 8 can be positioned in the drill support with the drill bit 9 aimed at the bit-hole 155 in the jig in the proximal direction 2, such as shown, for example, in FIGS. 5 and 6. The drill supports 120 ensure that the drill and the drill bit therein are maintained at a constant angle and position relative to the jig. A drill support allows the drill to be advanced towards the jig, as shown in FIGS. 5 and 6. There are a variety of drills known in the art, both manual and electric, for making burr-holes in a skull. Thus, the configuration of the drill support is not limited to use with any particular type, make, or brand of drill. In one embodiment, the drill support 105 is configured generically, so as to support a variety of drill types, makes, and brands.

The drill support 105 maintains the position of a drill. To ensure accuracy, the drill guide 100 can also have a jig 150, proximal to the drill support, with a bit-hole 155 for receiving the drill-bit and guiding it to the correct location on the skull. The bit-hole can have a diameter that is only slightly larger than the diameter of the drill-bit, which inhibits the drill-bit from straying off-center. Thus, the drill guide maintains the drill bit in alignment with the bit-hole in the post. The jig can also be customized to allow the drill bit to enter the skull and brain to a predetermined depth.

In one embodiment, the bit-hole can open onto the distal side 3 of the jig and extend through the jig to open onto the proximal side 2 of the jig. FIG. 6 shows an example of a bit-hole opening onto the distal side of the jig. With this embodiment, the jig can be placed against the skull guide with the bit-hole aligned with a pilot hole, so that the drill-bit can be advanced through the bit-hole and the pilot hole and into the skull. In one embodiment, the jig is configured to allow the drill bit to advance only as far as necessary to the burr hole depth required.

In a further embodiment, there is a post 160 that extends perpendicularly from the proximal side 2 of the jig. The bit-hole can continue through the post to open onto the proximal end 2 of the post. FIG. 4 shows an example of the bit-hole opening onto the proximal end 2 of a post extending from the jig. As shown in FIG. 5, the post can be inserted into one of the pilot holes 230 in the skull guide and the drill advanced proximally 2 through both the jig and the post to create the burr-hole. A pilot hole can have any of a variety of circumferential shapes such as, for example, round, square, triangular, hexagonal, or other geometric shape. In a further embodiment, the post is configured to form fit, match, coincide with the shape of or otherwise align with the shape of the pilot hole. This can simultaneously align the drill bit over the correct location for the burr hole. In a specific embodiment, the post is configured to center the drill bit in the pilot hole. The post can be moved to other pilot holes to create additional burr-holes as needed. The drill guide can then be removed from the skull guide. Thus, from the above description it will be understood that one or both of the skull guide and drill guide can be customized to subject and/or a specific procedure so that, when used together, the drill bit is directed to the exact location for making a burr-hole and the exact depth to drill the burr-hole to achieve intracranial access. In one embodiment, a post has a diameter of between about 7 mm and about 8 mm. In a specific embodiment, a post has a diameter of about 7.5 mm. A specific embodiment of a post has an outer diameter of about 7.5 mm.

Once the necessary one or more burr holes have been made in the skull, cranial implants can be inserted through the pilot holes in the skull guide and into the burr holes. As discussed above, the location of the burr holes can be accurately determined by analysis of tissue images. The burr hole is precisely drilled using a drill guide that aligns with a skull guide fixedly attached in an exact location on a skull. Proper insertion of a cranial implant in linear alignment with a pilot hole and a burr hole should position the cranial implant in the exact desired location in the tissue.

One advantage of the stereotactic system of the subject invention is that it allows cranial implants to be placed by hand with accuracy in placement. The interoperability of the skull guide and drill guide ensure example placement of the burr hole. The cranial implants can also be designed for interoperability with the skull guide.

Figures 7, 8, 9:
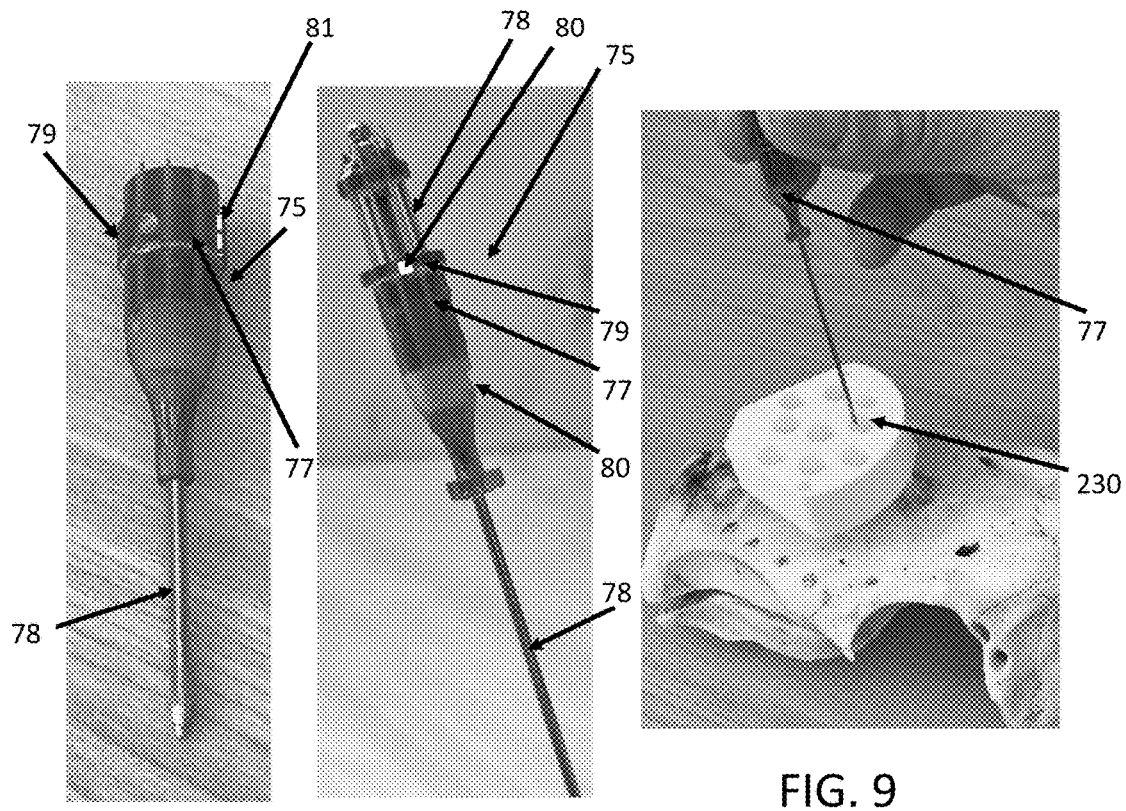
FIG. 7 shows an embodiment of an implant shuttle that can be used with embodiments of a skull guide, according to the subject invention.
FIG. 8 shows another embodiment of an implant shuttle that can be used with embodiments of a skull guide, according to the subject invention. The implant shuttle shown in FIG. 8 has drive screws that allow the implant to be driven deeper into the brain.
FIG. 9 shows an embodiment of a skull guide, according to the subject invention, affixed to a representative skull with an implant shuttle being inserted through one of the guide holes in the skull guide towards a burr hole drilled in the skull.

In one embodiment, an intracranial implant is configured as an implant shuttle 75 that is guided into the burr hole. In a further embodiment, an implant shuttle has a sheath 77 configured to have a shape that fits with, coincides to, matches the shape of, or otherwise aligns with a pilot hole in the skull guide. FIGS. 7 and 8 illustrate embodiments of implant shuttles. In a specific embodiment, the sheath has a larger diameter stopper 79 around the outside that abuts the rim of a pilot hole to control the depth to which the implant shuttle inserts into the burr hole, an example of which is shown in FIGS. 7 and 8. The stopper can include attachment mechanisms 81 for attaching the implant shuttles to the skull guide and/or attaching additional or secondary components to the implant shuttles, such as, for example, drive covers and electrode interface boards (EIB). Such attachment mechanisms can include, but are not limited to, clips, screws, mounts, surface extensions, and other devices or techniques known to those with skill in the art. The sheath or the stopper can also have one or more notches or that be used to control the rotation of the implant shuttle in the burr hole. Thus, an implant shuttle can be arranged in a specific position in the pilot hole and is supported by the walls of the pilot hole. FIGS. 7 and 8 show non-limiting examples of implant shuttles configured with a shape that allows it to be exactly placed within the pilot hole. Aligning the implant shuttle with the pilot hole can further ensure that the cranial implant is directed at the precise, desired tissue location. In one embodiment, an implant shuttle is a separate component that it can be joined with an intracranial implant. In a further embodiment, an implant shuttle is generic such that it can be joined with any of a variety of intracranial implants. In an alternative embodiment, an intracranial implant and an implant shuttle can be formed as a single, non-separable, unitary piece or unit. With this embodiment, an implant shuttle can be specific to the shape of the pilot holes in the skull guide. FIG. 9 illustrates an example of an implant shuttle being inserted through a pilot hole, such that it is aligned with the burr hole in the underlying skull. FIG. 10 illustrates the linear alignment of the pilot hole, burr hole, and implant shuttle in a skull. One embodiment of an intracranial implant configured as an implant shuttle utilizes a 32-channel 8-barrel tetrode electrophysiology recording array. This embodiment has sheath 77 with an outer diameter of about 7.5 mm.

At this point, in the method of the subject invention, the skull guide has been fixedly attached to the skull, burr holes have been made in the skull, and intracranial implants/implant shuttles have been positioned in the desired locations in the tissue through the skull guide pilot holes. The critical aspects of the procedure have been performed and testing can proceed. The stereotactic system 10 of the subject invention provides an advantageous, all-in-one chronic implant system for use with large animals. Thus, after completion of a testing regimen, the implants remain in place and the animal is allowed to move about in normal behavior. It can be beneficial to the animal and future testing if the implants are protected where they protrude from the skull.

Embodiments of the stereotactic system of the subject invention include a NeuroHat device (or "NeuroHat") designed to attach to the skull guide 200 to protect, and provide access to, the implant shuttles 75 or other intracranial implants. A NeuroHat can include a lower housing 300, with a mounting socket 400, and an upper housing 500. When combined over a skull guide, the NeuroHat can inhibit the effects of collisions or other contact with the intracranial implants. The NeuroHat is also directed posteriorly, or towards the neck of the animal, which can further inhibit contact and permit easier access to the intracranial implants and other areas of the NeuroHat.

Figure 11:
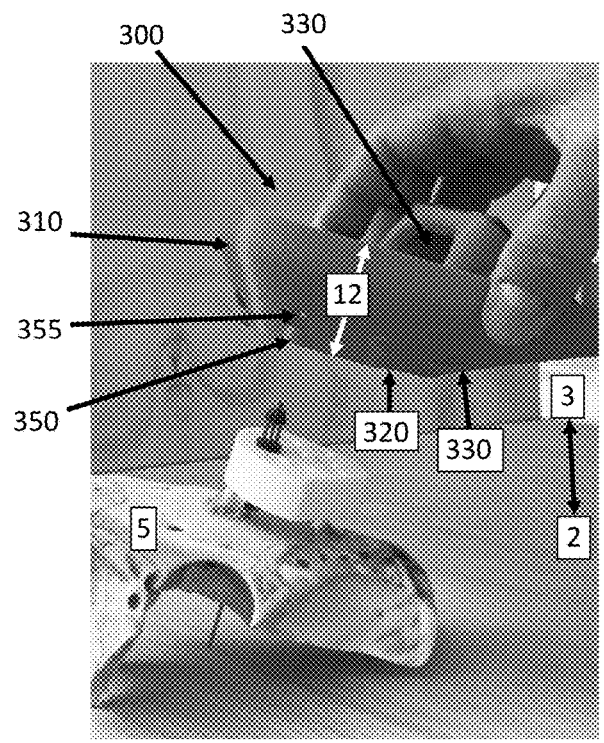
FIG. 11 shows an embodiment of a lower-housing, according to the subject invention, prior to arrangement on the skull guide and electrode, shown in FIG. 10.
Figure 12:
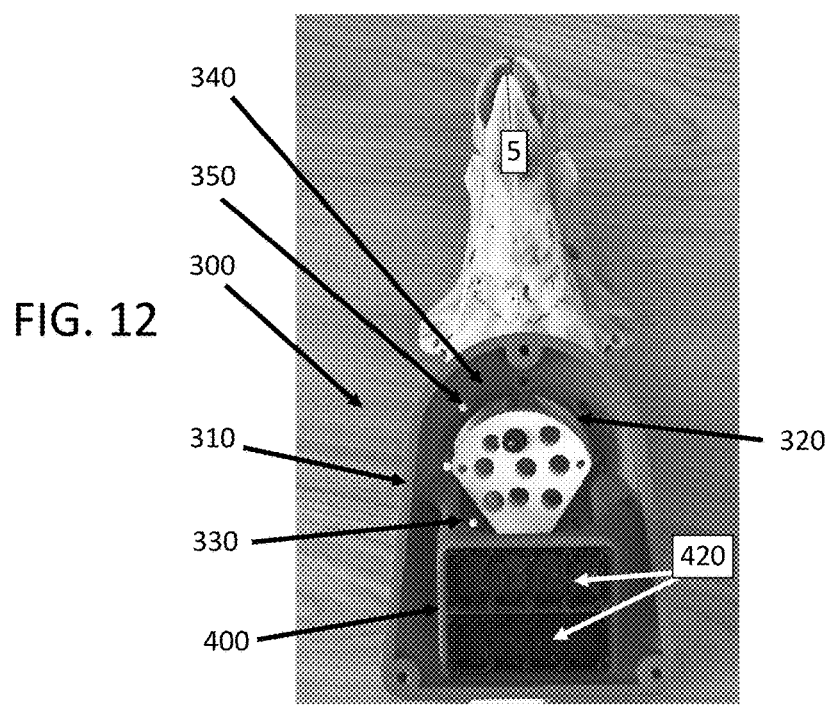
FIG. 12 shows an embodiment of a lower-housing, according to the subject invention, arranged on the skull guide and electrode, shown in FIG. 10.

The skull guide 200, being fixedly attached to the skull 5, provides a point of contact to which the components of a NeuroHat can be connected. The first component that can be connected to the skull guide is the lower housing 300, which is shown, by way of example, in FIG. 11. In one embodiment, the lower housing has a bowl-like shape with sidewalls 310 that rise distally 3 from a base 320 that has an aperture 330 therethrough. It can be seen in FIG. 12 that the aperture provides an access opening for inserting the skull guide in the lower housing. The aperture can have any number of configurations, depending upon the shape and configuration of the skull guide. FIGS. 11 and 12 show one embodiment where the aperture is a slot-like opening in which the skull guide can be slid into the lower housing from the posterior end. This can allow the base of the housing to slide under the edges of the skull guide, as shown in FIG. 12. Other aperture 330 arrangements can also be used that allow the lower housing to be positioned around the skull guide. When the skull guide slides through the aperture, it will be positioned within a chamber 340 in the lower housing, as shown, for example, in FIG. 12

In one embodiment, the height 12 of the sidewalls 310 of a lower housing rises higher than at least the distal side 3 of the fixedly attached skull cap. Thus, when emplaced the lower housing surrounds the entire skull guide. In another embodiment, the height of the sidewalls 310 rises higher than at least the distal end of any intracranial implant situated in the skull guide. Thus, when emplaced, the lower housing surrounds the entire skull guide and the intracranial implants rising above the skull guide.

The lower housing can also be secured to the skull 5. In one embodiment, the lower housing 300 has at least one hole 350 in the base through which skull screws can be inserted and affixed to the skull. In more particular embodiment, the lower housing has between about 8 and about 20 holes through which skull screws can be inserted and affixed to the skull. FIG. 12 shows an example of holes that can be accessed from within the chamber 340. The skull screws can be further secured with an adhesive. In a further embodiment, the lower housing has side ports 355 in communication with the openings 350 in which an adhesive, such as, for example, methyl methacrylate, can be deposited into the openings to occupy space on the inside and outside of the base and/or secure a skull screw in the hole. FIG. 11 shows an example of side ports on the outside of the lower housing that provide access to a hole.

In a further embodiment, the lower housing includes a mounting socket 400. The mounting socket allows for the attachment of various secondary devices 7 to the lower housing. The mounting socket can further have a plurality of conformations 420 for attachment of secondary devices. Intracranial implants can be attached directly or indirectly to various secondary devices 7 that receive information (e.g., electrical impulses) from the intracranial implants. In one embodiment, there can be multiple pin set female plugs operably connected (e.g., wired) to electrodes 78 carried on the cranial implants or implant shuttles 75. In a further embodiment, cables can be attached to the electrodes and run to the mounting socket to one of the plugs. The secondary devices, when attached to the mounting socket, can connect to one or more of the plugs and the cable therein.

In one embodiment, the mounting socket is accessible from the outside of the NeuroHat. As explained below, the upper housing can surround the mounting socket. In one embodiment, illustrated in FIG. 11, the mounting socket rises above the height of the side walls 310 of the lower housing 300. In a further embodiment, the upper housing 500, as explained below, goes around the mounting socket so as to not interfere with access thereto. FIGS. 1 and 2 illustrate a non-limiting example of a mounting socket that is accessible from the outside of the NeuroHat and to which a secondary device has been attached to connect to the internal conformations.

Figure 13:
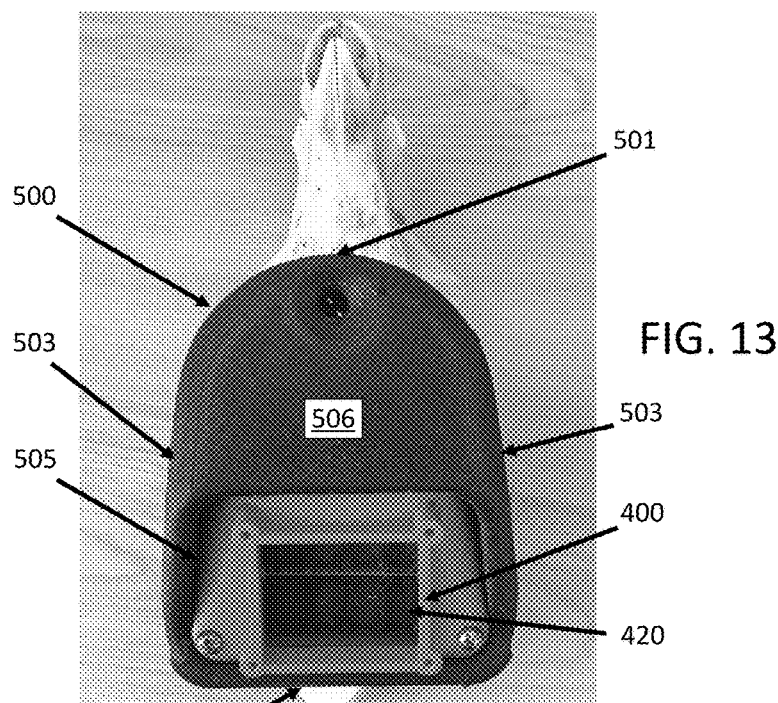
FIG. 13 shows an embodiment of an upper-housing, according to the subject invention, arranged on a lower-housing to complete a NeuroHat stereotactic device. Here, the mounting socket is shown with the access plate removed.
Figure 14:
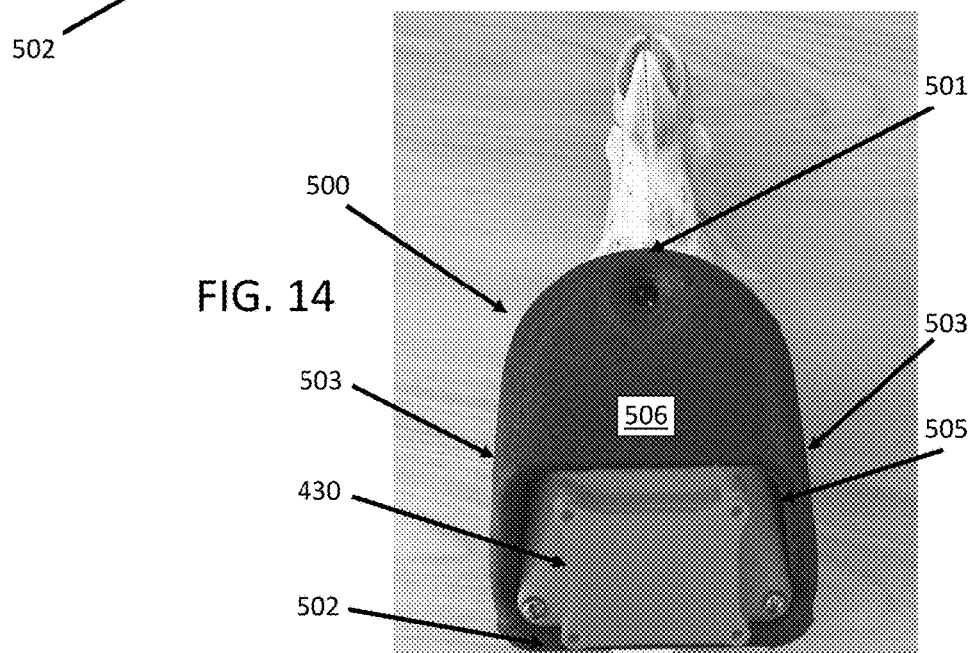
FIG. 14 shows an embodiment of an upper-housing, according to the subject invention, arranged on a lower-housing to complete a NeuroHat stereotactic device. Here, the mounting socket is shown with the access plate installed.

Arranged on the lower housing 300 can be an upper housing 500, as shown, by way of example, in FIGS. 1, 13 and 14. In one embodiment, the upper housing goes around or encircles the a periphery of the distal end 3 of the sidewalls of the upper housing so that at least a portion of the height 8 of the sidewalls of the lower housing is surrounded. Thus, the upper housing has an orifice 505 in which the mounting socket can reside when the upper housing 500 is positioned over the lower housing 300. With this embodiment, there is an anterior section 501, a posterior section 502, and two lateral sections 503, which are all joined to encircle the sidewalls of the upper housing. Thus, the upper housing can go down over to encircle the lower housing, and cover at least a distal end 3 portion of the sidewalls, such that the upper housing does not extend fully to the proximal end 2 of the lower housing. FIGS. 13 and 14 illustrate an example of an upper housing that encircles the sidewalls and covers a portion of the height of the sidewalls and the proximal end 2 of the lower housing is still uncovered and visible.

In an alternative embodiment, an upper housing 500 goes around or encircles part or some portion of the periphery of the sidewalls of the upper housing, so that at least a portion of the height 8 of the sidewalls of the lower housing is surrounded. With this embodiment, the upper housing is C-shaped, such that there is an anterior section 501, but at least one of the posterior section 502 or a lateral section 503 may not be present. The sections that are present encircle some portion of the periphery of the sidewalls of the upper housing. Thus, the upper housing can still encircle a portion of the distal end of the lower housing sidewalls, such that the upper housing does not extend fully around the periphery of the sidewall and does not extend to the proximal end 2 of the lower housing. One non-limiting example of this embodiment is shown in FIG. 4, which illustrates an example of an upper housing with an anterior section 501 and two lateral sections, but does not have a posterior section, so that the upper housing encircles part of the sidewalls goes over a portion of the height of the sidewalls leaving the proximal end 2 of the lower housing still uncovered and visible.

The chamber 340 of the lower housing can contain the skull guide and, when implanted, one or more implant shuttles 75, as described above. In one embodiment, the upper housing 500 has a cover section 506 that extends over the distal side 3 of the upper housing. In a specific embodiment, the cover section extends over an anterior section 501 of the chamber 340, and ends just to the anterior side of the mounting socket 400, as shown, for example, in FIG. 2. With this embodiment, the cover section will be over or above the skull guide 200, so as to protect the underlying intracranial implants 75 fitted into the skull guide, but will not interfere with the attachment of secondary devices to the mounting socket.

The upper housing can be attached to the lower housing. Preferably, the upper housing is removably attached to the lower housing. The upper housing can be attached by any of a variety of attachment devices 15 and techniques known to those with skill in the art. For example, FIG. 12 illustrates a lower housing with one or more screw holes for attachment to the upper housing with screws. FIG. 4 illustrates an upper housing attached to a lower housing with a snap or pressure latch. Thus, the invention is not limited to the attachment device used to attach the upper housing to the lower housing.

The use of animal subjects for neurophysiological studies presents challenges in implanting and maintaining intracranial implants. Chronic studies with implants must allow the animals to enjoy normal activity and behavior when not under examination. The subject invention provides a unique and advantageous device for both accurately implanting and maintaining intracranial implants. By providing customized and interoperable components, implants can be emplaced by hand and reduces the number of measurements and adjustments during the implantation procedure. The NeuroHat requires minimally invasive installation, which improves survivability of the animal subjects. The stereotactic device of the subject invention represents a significant improvement in current neurosurgical procedures.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A stereotactic system, adapted for attachment to the skull of a subject, comprising:
   a skull guide with a plurality of pilot holes and at least two stand-off posts for attachment to the skull;
   one or more implant shuttles, for insertion into the pilot holes, comprising a sheath that aligns with and is supported by the pilot hole and an electrode; and
   a stereotactic device that engages with the skull guide, the stereotactic device comprising:
      a lower housing with sidewalls and an aperture that leads into a chamber, such that the skull guide is inserted into the chamber through the aperture;

a mounting socket configured on the lower housing having one or more conformations, adapted to attach a secondary device to the implant shuttles; and an upper housing for placement over the lower housing with a cover section that extends over the chamber and an orifice for receiving the mounting socket therethrough.

2. The stereotactic system, according to claim 1, further comprising:
a drill guide having:
a drill support, adapted to receive and support a drill; and
a jig, proximal to the drill support, that includes a post on a proximal side of the jig that engages with a pilot hole in the skull guide and is adapted to guide a drill bit through the pilot hole.

3. The stereotactic system, according to claim 1, further comprising a plurality of conformations in the mounting socket to which the electrodes of the implant shuttles are operably attached.

4. The stereotactic system, according to claim 3, further comprising at least one hole in the lower housing adapted to receive a skull screw for attachment of the lower housing to the skull.

5. The stereotactic system, according to claim 4, further comprising a side port in communication with the hole.

6. The stereotactic system, according to claim 3, the skull guide being customized for attachment to the skull of the subject.

7. The stereotactic system, according to claim 6, at least one of the length and position of at least one of the plurality of pilot holes and the at least two stand-off posts being customized for attachment to the skull of the subject.

8. The stereotactic system, according to claim 1, wherein the sidewalls of the lower housing rise to at least the height of the distal end of an implant shuttle inserted into a pilot hole in the skull guide.

9. The stereotactic system, according to claim 1, further comprising enhancement on the at least two stand-off posts of the skull guide to aid in securing the stand-off posts to the skull.

10. The stereotactic system, according to claim 9, further comprising:
a drill guide having:
a drill support, adapted to receive and support a drill; and
a jig, proximal to the drill support, that includes a post on a proximal side of the jig that engages with a pilot hole in the skull guide and is adapted to guide a drill bit through the pilot hole.

11. A method for implanting intracranial implants, adapted to be inserted through a skull, the method comprising:
providing the stereotactic system according to claim 1;
attaching to the skull a skull guide fixedly attaching to the skull the at least two stand-off posts;
making at least one burr hole in the skull utilizing a drill guide comprising:
a drill support, adapted to receive and support a drill; and
a jig, proximal to the drill support, that includes a post on a proximal side of the jig that engages with a pilot hole in the skull guide and is adapted to guide a drill bit through the pilot hole and into the skull;
removing the drill guide from the skull guide; and
inserting an intracranial implant configured with the sheath and the electrode into the pilot hole so that the sheath is supported by the pilot hole and the electrode aligns with and passes through the burr hole.

12. The method, according to claim 11, further comprising customizing the skull guide to align to specific coordinates in the anterior-posterior and medial-lateral directions of the skull.

13. The method, according to claim 12, customizing the skull guide including configuring the position and length of the at least two posts.

14. The method, according to claim 11, further comprising:
positioning on the skull guide the lower housing, by inserting the skull guide into the chamber through the aperture, and
positioning the upper housing over the lower housing, such that the cover section on the upper housing extends over the chamber; and
attaching the upper housing to the lower housing.

15. The method, according to claim 14, further comprising at least one hole in the lower housing, adapted to receive a skull screw, the method further comprising attaching the lower housing to the skull utilizing a skull screw through the at least one hole.

16. The method, according to claim 15, further comprising a side port in communication with the at least one hole, the method further comprises applying an adhesive through the side port to further secure the skull screw in the at least one hole.

17. The method according to claim 15, further comprising attaching the upper housing so that the mounting socket extends through the orifice.

18. The method, according to claim 11, further comprising a stopper on the sheath of the intracranial implant and one or more attachment mechanism on the stopper and the method further comprises attaching one or more secondary components to the intracranial implant utilizing the attachment mechanism.

19. A stereotactic system, adapted for attachment to the skull of a subject, comprising:
a skull guide with a plurality of pilot holes and at least two stand-off posts for attachment to the skull;
one or more implant shuttles, for insertion into the pilot holes, comprising a sheath that aligns with and is supported by the pilot hole, an electrode, and stopper for controlling the depth of the electrode, and one or more attachment mechanisms on the stopper for attachment of secondary components; and
a stereotactic device that engages with the skull guide, the stereotactic device comprising:
a lower housing with sidewalls, an aperture at the posterior end that leads into a chamber, such that the skull guide is inserted into the chamber through the aperture, at least one hole by which the lower housing is attachable to the skull, and a side port in communication with the at least one hole;
a mounting socket configured on the lower housing comprising one or more conformations, adapted to attach a secondary device to the one or more implant shuttles, and a removable access plate for covering the conformations; and
an upper housing for placement over the lower housing that at least partially surrounds the lower housing sidewalls, a cover section at the anterior end that extends over the chamber and an orifice at the posterior end through which the mounting socket extends distally therethrough, wherein the sidewalls of the lower housing rise to at least the height of the distal end of an implant shuttle inserted into a pilot hole in the skull guide, wherein the stereotactic system further comprises enhancement on the at least two standoff posts of the skull guide to aid in securing the standoff posts to the skull, and wherein the stereotactic system further comprises a drill guide having:
- a drill support, adapted to receive and support a drill; and
- a jig, proximal to the drill support, that includes a post on a proximal side of the jig that engages with a pilot hole in the skull guide and is adapted to guide a drill bit through the pilot hole.

* * * * *